(12) United States Patent
Volpicelli et al.

(10) Patent No.: US 7,960,572 B2
(45) Date of Patent: Jun. 14, 2011

(54) PROCESS FOR PREPARING NEBIVOLOL

(75) Inventors: Raffaella Volpicelli, Vicenza (IT); Paolo Maragni, Virgilio (IT); Livius Cotarca, Cervignano del Friuli (IT); Johnny Foletto, Arcole (IT)

(73) Assignee: Zach System S.p.A., Bresso (Milano) (IT)

( * ) Notice: Subject to any disclaimer, the term of this patent is extended or adjusted under 35 U.S.C. 154(b) by 215 days.

(21) Appl. No.: 12/443,279

(22) PCT Filed: Oct. 2, 2007

(86) PCT No.: PCT/EP2007/008549
§ 371 (c)(1),
(2), (4) Date: Mar. 27, 2009

(87) PCT Pub. No.: WO2008/040528
PCT Pub. Date: Apr. 10, 2008

(65) Prior Publication Data
US 2010/0069652 A1    Mar. 18, 2010

(30) Foreign Application Priority Data
Oct. 3, 2006   (IT) ............... MI2006A1889

(51) Int. Cl.
*C07D 311/20*   (2006.01)
(52) U.S. Cl. .............. 549/398; 549/405; 549/407
(58) Field of Classification Search .............. 549/398, 549/405, 407
See application file for complete search history.

(56) References Cited

U.S. PATENT DOCUMENTS
7,560,575 B2 *   7/2009   Bader et al. .............. 549/407

FOREIGN PATENT DOCUMENTS

| | | |
|---|---|---|
| EP | 0145067 A1 | 6/1985 |
| EP | 0334429 A1 | 9/1989 |
| EP | 1803715 A1 | 7/2007 |
| WO | 2004004185 A1 | 5/2004 |
| WO | 2006016376 A1 | 2/2006 |
| WO | 2006025070 A1 | 3/2006 |

OTHER PUBLICATIONS

Chandrasekhar, et al., Enantiomer Total Synthesis of the Antihypertensive Agent (S,R,R,R)-Nebivolol, vol. 56, No. 34, 2000-08-18, pp. 6339-6344, Tetrahedron, Elsevier Science Publishers, Amsterdam, NL.

Written Opinion of the International Searching Authority issued for the corresponding PCT International Application No. PCT/EP2007/008549.

* cited by examiner

*Primary Examiner* — Bernard Dentz
(74) *Attorney, Agent, or Firm* — Lucas & Mercanti, LLP

(57) ABSTRACT

The present invention relates to a process for the preparation of Nebivolol and, more particularly, to an improved method of synthesizing 6-fluoro chroman epoxides of formula (I) key intermediates in preparing nebivolol.

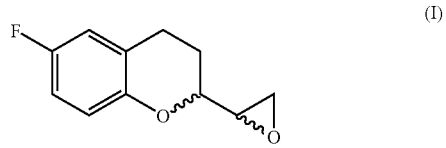

18 Claims, No Drawings

PROCESS FOR PREPARING NEBIVOLOL

CROSS REFERENCE TO RELATED APPLICATIONS

This application is the United States national phase filing of the corresponding international application number PCT/EP2007/008549, filed on Oct. 2, 2007, which claims priority to and benefit of Italian application number MI2006A001889, filed Oct. 3, 2006, which applications are hereby incorporated by reference in their entirety.

The present invention relates to a process for the preparation of Nebivolol and, more particularly, to an improved method of synthesizing 6-fluoro chroman epoxides of formula

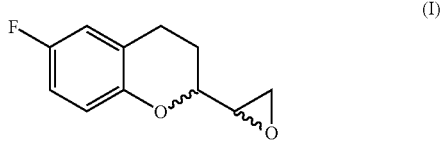

(I)

key intermediates in preparing nebivolol.

Nebivolol (hereafter NBV), is a mixture of equal amounts of [2S[2R*[R[R*]]]]α,α'-[imino-bis(methylene)]bis[6-fluoro-chroman-2-methanol] (hereafter d-NBV) of formula (IA)

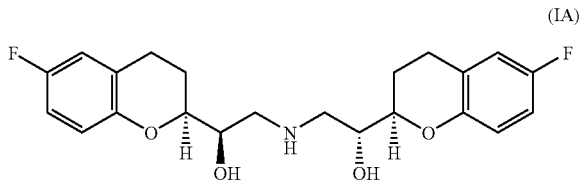

(IA)

and its [2R[2S*[S[S*]]]]enantiomer (hereafter l-NBV) of formula (IB)

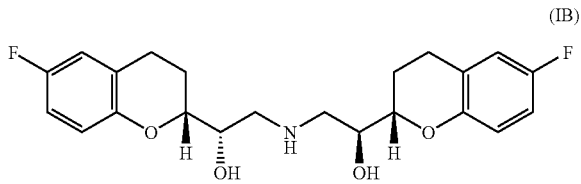

(IB)

Nebivolol is characterised by its β-adrenergic blocking properties and is useful in treating essential hypertension. It has basic properties and may be converted into its addition salts through treatment with suitable acids. The hydrochloric acid addition salt is the marketed product.

It is known in the art that the synthesis of α,α'-[imino-bis(methylene)]bis[chroman-2-methanol] molecular structures is challenging for the skilled person because of the 4 asymmetric carbon atoms producing a mixture of 16 stereoisomers (in case of asymmetrical substitutions) or a mixture of 10 stereoisomers (in case of symmetrical substitutions). As apparent from the presence of symmetry in the nebivolol structure, a total of 10 stereoisomers may be generated.

Literature reports several processes for the preparation of nebivolol.

The patent EP 145067 describes a method of preparing NBV which comprises synthesizing diastereoisomeric mixtures of chroman epoxide derivatives in accordance with the synthetic scheme below

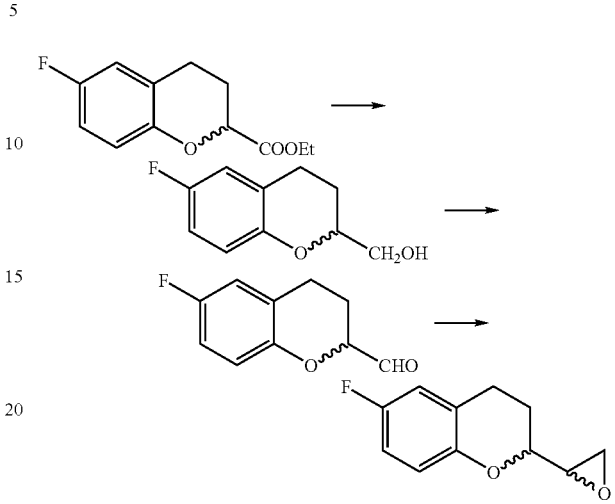

The 6-fluoro chroman carboxylic acid ethyl ester, derived from the esterification of the corresponding acid, is reduced with sodium dihydro bis-(2-methoxyethoxy)-aluminate to primary alcohol; the product is reacted with oxalyl chloride and then triethylamine at −60° C. to give the corresponding racemic aldehyde, which is then converted into epoxide as a mixture of (R,S), (S,R), (R,R) and (S,S) stereoisomers.

Said epoxide derivatives represent the key intermediates of the process.

The patent EP 334429 mainly describes the same synthetic process reported in the previous patent and is, particularly, directed to the preparation of single optical isomers (R,S,S,S) and (S,R,R,R) of NBV.

In this instance, the 6-fluoro chroman carboxylic acid is resolved into single enantiomers by treatment with (+)-dehydroabiethylamine. Said single enantiomers are separately converted into their corresponding epoxides resulting in a mixture of two diastereoisomers. The following synthetic scheme describes, for example, the conversion of the S-acid derivative.

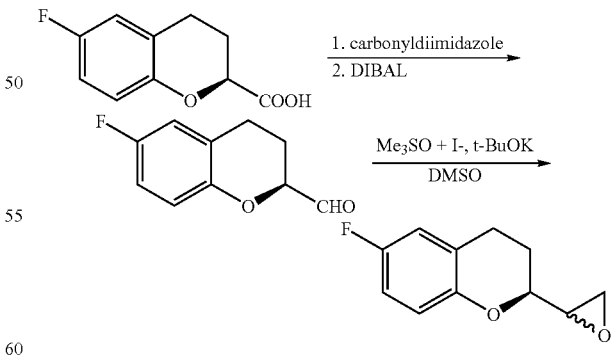

Nevertheless, both the above mentioned synthetic methods suffer from several drawbacks with regard to the industrial application of the process.

In particular, the conversion of the chroman acid or its ester derivative with epoxide nucleus involves the formation of the corresponding 6-fluoro chroman aldehyde.

The aldehyde is usually prepared at very low temperatures (−60° C.), under conditions that require special equipments in the production plants.

It is known in the art that this intermediate has remarkable problems in terms of chemical instability and, moreover, it has been shown that it can lead to degradation by-products undesirable at synthetic level.

According to international patent application WO 2004/041805, the aldehyde product obtained by means of distillation can not be used in the synthetic process after standing a night at room temperature because of disintegration problems.

Furthermore, the racemic aldehyde is in the form of an oil that is difficult to handle and that has an high tendency towards polymerisation.

In addition, yields of chroman epoxide obtained by using the above processes, based on the 6-fluoro chroman carboxylic acid substrate, are very low.

Literature describes stereoselective methods for the preparation of l-NBV and d-NBV and some alternative total syntheses; see, for example, international patent applications WO 2004/041805, WO 2006/016376 and WO 2006/025070.

Therefore, the essential role of the 6-fluoro-chroman epoxide compound in preparing NBV is known and it would be desirable to study alternative methods for preparing the intermediate of formula I in racemic form or in its single stereoisomers, which allow said intermediate to be prepared with good yields and under conditions more favourable from the process industrial application point of view.

We have now, surprisingly, found an improved process for synthesizing 6-fluoro-chroman epoxides, key intermediates in preparing nebivolol, which allow to overcome the drawbacks of the processes described in the prior art.

Therefore, a first object of the present invention is a process for preparing a compound of formula

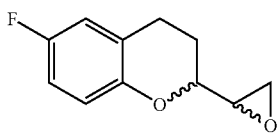

which comprises
a. the conversion of a compound of formula

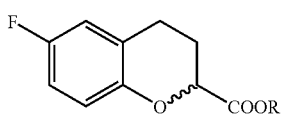

wherein R is a $(C_1-C_6)$-alkyl group, optionally substituted aryl or optionally substituted heteroaryl; in a compound of formula

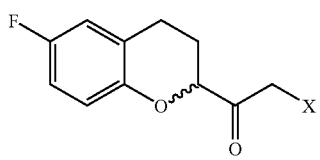

where X is halogen;

b. the reduction of a compound of formula II to give a compound of formula

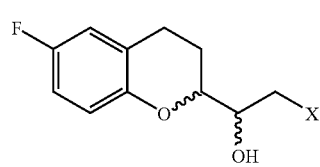

c. the reaction of said compound of formula III with a base to give the epoxide compound of formula I.

The reduction of a compound of formula II to give a compound of formula III (step b) is carried out according to known techniques.

Generally, the reduction of ketone group is carried out with reducing agents such as, for example, sodium borohydride or lithium aluminium hydride and derivatives thereof such as, for example, lithium dimesityl borohydride bis-dimethoxymethane, in alcoholic and etheric solvents. Reducing agents, such as boranes and borates are useful in the reduction of chloroketones.

The reduction of ketone group may also be carried out by catalytic hydrogenation in solvents such as alcohols, and their aqueous mixtures optionally under CTH conditions (catalyzed transfer hydrogenations) i.e. by generating hydrogen in situ from suitable substrates such as ammonium formiate, formic acid and cyclohexadiene. Preferred homogenous catalysts for the transformation are rhodium, ruthenium, iridium and palladium complexes.

Preferably, the reaction is carried out by reacting a compound of formula II with sodium borohydride in the presence of an alcoholic solvent, optionally mixed with water. Preferred solvent is ethanol.

The reaction of a compound of formula III to give a compound of formula I (step c) is carried out in the presence of a base in accordance with known techniques.

Suitable bases in the formation of the epoxide nucleus are, for example, alkaline hydroxides or alkoxides and amines, preferably, alkaline hydroxides or alkoxides.

Suitable solvents in the formation of the epoxide nucleus are, for example, alcohols or ethers or their aqueous mixtures.

The epoxidization is preferably carried out by reacting a compound of formula III with alkaline alkoxides or hydroxides in the presence of alcoholic solvents or ethers optionally in admixture.

A preferred embodiment of the invention is that the reaction is carried out with a base such as potassium t-butoxide in the presence of an isopropanol/THF mixture.

Alternatively, the reaction is carried out with a base such as sodium hydroxide in the presence of isopropanol.

A further preferred embodiment of the invention foresees the reduction of chloroketone to chlorohydrin according to one of the above-mentioned methods and a one-pot epoxidization by adding suitable bases to the reduction mixture.

In the present invention under the term halogen a fluorine, chlorine, bromine and iodine atom are meant.

X is preferably a chlorine atom.

In the present invention R is preferably a $(C_1-C_6)$-alkyl group or optionally substituted phenyl.

The compound 2-halo-chroman ethanone of formula II is prepared by subjecting the chroman nucleus to some of the procedures known in the art for the conversion of carboxylic acids or their derivatives, particularly esters, in the corresponding alpha-haloketones.

The compounds of formula IV are known intermediates in the preparation of NBV, whose preparation is extensively described in the art, see, for example, the above cited patent EP 145067.

The conversion of a compound of formula IV into a compound of formula II (step a) is possible, for example, via diazo compounds, via carbenoid intermediates, via Claisen condensation or via sulfoxonium ylide in accordance with procedures known to the skilled person.

Generally, said conversion is carried out by reacting a compound of formula IV with a sulfoxonium ylide, for example, dimethylsulfoxonium methylide to give the corresponding keto sulfoxonium ylide, which is transformed into an alpha-haloketone of formula II by reaction with anhydrous halogenhydric acids optionally generated in situ.

Said sulfoxonium ylide is preferably prepared from the corresponding sulfoxonium salt by reaction with a suitable base, such as, for example, sodium hydride, potassium t-butoxide and potassium t-amylate in the presence of an organic solvent such as, for example, tetrahydrofuran, toluene and DMF.

Preferably, a compound of formula IV is reacted with dimethylsulfoxonium methylide, prepared in situ from trimethylsulfoxonium iodide and potassium t-butoxide in the presence of THF, to give the corresponding keto sulfoxonium ylide of formula

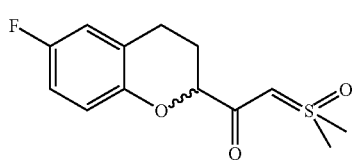

(V)

which is transformed into a compound of formula II, wherein X is a chlorine atom by reaction with anhydrous hydrochloric acid generated in situ by reacting lithium chloride with methanesulfonic acid in the presence of THF.

In the main, the methods of converting esters into alpha-haloketones should be stereoconservative for substrates with chiral centres in alpha with regard to the ester function.

Therefore, it seems evident to the skilled person how the application of the process object of the invention to enantiomerically pure substrates, such as chroman acid nuclea or resolved esters, leads to the formation of epoxide derivatives in racemic form comprising a mixture of two diastereoisomers.

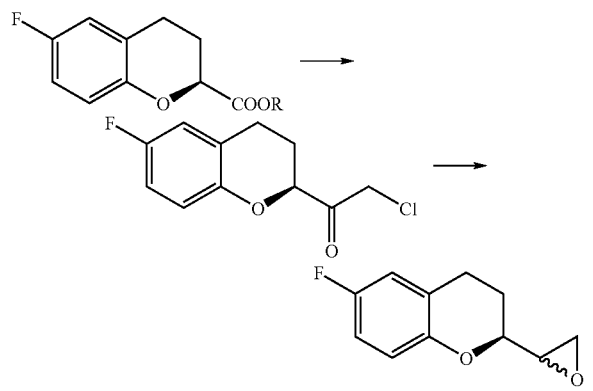

As known, said partially resolved epoxide derivatives represent key intermediates in the preparation of NBV.

A further object of the present invention is a process for preparing a compound of formula

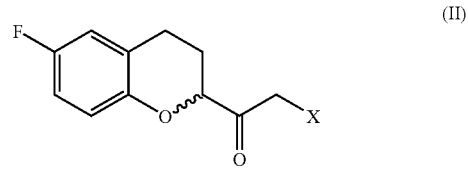

(II)

where X is halogen;
which comprises reacting a compound of formula

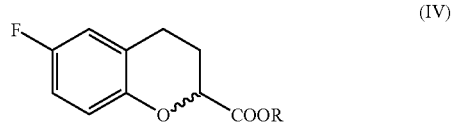

(IV)

wherein R is a $(C_1-C_6)$-alkyl group, optionally substituted aryl or optionally substituted heteroaryl; with dimethylsulfoxonium methylide to give the corresponding keto sulfoxonium ylide of formula

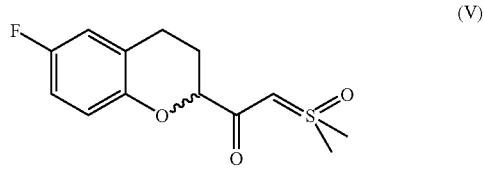

(V)

which is converted into a compound of formula II by reaction with an anhydrous halogenhydric acid optionally generated in situ.

A further object of the present invention is a process for synthesizing nebivolol, characterised by the fact that the preparation of a compound of formula

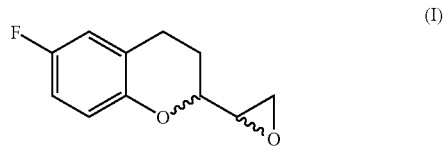

(I)

comprises
a. the conversion of a compound of formula

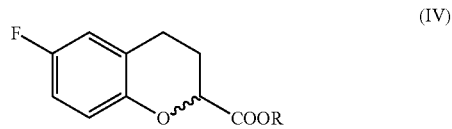

(IV)

wherein R is a $(C_1-C_6)$-alkyl group, optionally substituted aryl or optionally substituted heteroaryl; in a compound of formula

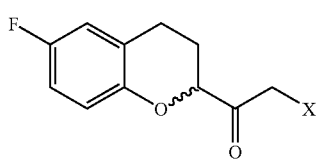

(II)

where X is halogen;

b. the reduction of a compound of formula II to give a compound of formula

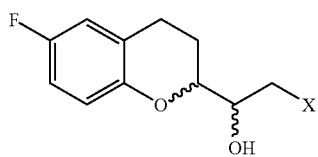

(III)

c. the reaction of said compound of formula III with a base to give the epoxide compound of formula I.

The process object of the present invention uses substrates that are easily found on the market, thus avoiding the use of carbonyldiimidazole and expensive reducing agents such as diisobutyl aluminium hydride (DIBAL).

Nevertheless, the most relevant inventive aspect that may be linked to the process of the invention is, undoubtedly, the opportunity to bypass the route leading to chroman aldehyde; it is, in fact, known that one of the greatest drawbacks of the processes described in the art lies in the complex preparation and handling of said aldehyde intermediate.

It is thus evident how the method object of the invention constitutes an efficient and economic synthetic alternative in the preparation of chroman epoxides; in addition, the availability of the raw materials used, together with the reduced number of synthetic steps and the good yields obtained, give notable benefits in terms of process costs and efficiency.

A further object of the present invention is the compound of formula V: dimethylsulfoxonium-2-(6-fluoro-3,4-dihydro-2H-chromen-2-yl)-2-oxoethylide; as intermediate useful in the preparation of nebivolol.

A practical embodiment of the process object of the present invention comprises the conversion of a 6-fluoro chroman carboxylate of formula IV into an alpha-haloketone of formula II via sulfoxonium ylide; said alpha-haloketone of formula II is reduced to a halohydrin of formula III and cyclised to an epoxide derivative of formula I in the presence of a base.

A preferred practical embodiment of the process object of the present invention comprises the conversion of a 6-fluoro chroman carboxylate of formula IV into corresponding alpha-haloketone of formula II by reacting said carboxylate with dimethylsulfoxonium methylide, optionally prepared in situ, to give corresponding keto sulfoxonium ylide of formula V which, in turn, is reacted with anhydrous hydrochloric acid also optionally generated in situ; said alpha-chloroketone of formula II is reduced to a chlorohydrin of formula III by means of a reaction with sodium borohydride in the presence of an alcoholic solvent and cyclised to a epoxide derivative of formula I by reacting with alkali alkoxides or hydroxides in the presence of alcoholic solvents or ethers optionally in admixture.

For better illustrating the invention the following examples are now given.

EXAMPLE 1

Synthesis of methyl 6-fluoro-3,4-dihydro-2H-chromen-2-carboxylate

Acid 6-fluoro-3,4-dihydro-2H-chromen-2-carboxylic (10.0 g, 51.0 mmol, 96.8 A %) was dissolved in MeOH (50 ml) under nitrogen at 20° C. To the stirred solution was added $H_2SO_4$ (0.51 g, 5.0 mmol, 96.0%) and the mixture heated to 60° C. in 15 min.

After 3 hours under stirring at 60° C., the reaction was cooled to 25° C. in 15 min. and concentrated under vacuum to half volume (25 ml). A 5% aqueous solution of $NaHCO_3$ (50 ml) was added to the residue, followed by ethyl acetate (100 ml). The strata were separated and the organic phase dried on $Na_2SO_4$, filtered and concentrated at reduced pressure to give methyl 6-fluoro-3,4-dihydro-2H-chromen-2-carboxylate as a pale yellow oil (9.41 g, 87.9% yield, 96.8 A %).

$\delta_H$(400 MHz; $CDCl_3$) 6.89-6.79 (2H, m, Ar), 6.77-6.76-6.72 (1H, m, Ar), 4.73-4.69 (1H, m), 3.79 (3H, s), 2.87-2.69 (2H, m), 2.31-2.12 (2H, m).

EXAMPLE 2

Synthesis of dimethylsulfoxonium-2-(6-fluoro-3,4-dihydro-2H-chromen-2-yl)-2-oxoethylide A solution of potassium tert-butoxyde 1.0 M in THF (15 ml, 15.0 mmol) was added under nitrogen at 25° C. to a suspension of trimethylsulfoxonium iodide (3.30 g, 15.0 mmol) and THF (10 ml) in a 10 min. interval, with no visible light. The suspension was then heated to 70° C. for 2 hours and the reaction mixture cooled to 20° C. The reactor was loaded with a solution of methyl 6-fluoro-3,4-dihydro-2H-chromen-2-carboxylate (1.05 g, 4.14 mmol, 82.9 A %) in THF (2 ml) in 30 min. by using an injection pump. At addition completed the syringe was then washed with further THF (1 ml). After 3 hours under stirring at 20° C., demi water (10 ml) was added to the reaction mixture, which was kept under stirring for further 16 hours. The reaction mixture was then diluted with demi water (10 ml) and the volatile substances removed at reduced pressure at 25-30° C. Demi water (10 ml) and ethyl acetate (20 ml) were added to the residue and the strata separated. The aqueous stratum was then extracted with ethyl acetate (2×20 ml) and the collected organic strata were then dried with anhydrous sodium sulphate, filtered and concentrated under vacuum to give raw sulphur ylide as a pale yellow solid (1.10 g, 96% yield, 97.9 A %).

δH(400 MHz; CDCl3) 6.83-6.79 (2H, m, Ar), 6.77-6.72 (1H, m, Ar), 4.92 (1H, bs), 4.45-4.39 (1H, m), 3.48 (6H, bs), 2.85-2.68 (2H, m), 2.29-2.21 (1H, m), 2.10-1.99 (1H, m); m/z (EI) 270.072598 (M+.C13H15FO3S requires 270.07252).

bs=broad singlet.

EXAMPLE 3

Synthesis of 4-nitrophenyl 6-fluoro-3,4-dihydro-2H-chromen-2-carboxylate

A 50 ml rbf was charged with 6-fluoro-3,4-dihydro-2H-chromen-2-carboxylic acid (10.0 g, 51.0 mmol), oxalyl chloride (9.71 g, 76.5 mmol) and dichloromethane (24.9 g) under nitrogen atmosphere at room temperature. The mixture was stirred for 17 h at room temperature and then concentrated in vacuo at 30° C. The residue was dissolved in toluene (75 ml) and stirred at rt. 4-nitrophenol (7.05 g, 51.02 mmol) was added to the reaction mixture, followed by pyridine (5 ml)

over the period of 5 min. The slurry was heated to 80° C., stirred for 3 h at this temperature and then cooled to 25° C. The solid was separated by filtration and the filtered solution washed with 2M aqueous sodium hydroxide (65 g), with a saturated solution of sodium bicarbonate (2×51 g), and with demi water (53 g). The separated organic phase was concentrated in vacuo and dried via azeotropic distillation to furnish 4-nitrophenyl 6-fluoro-3,4-dihydro-2H-chromen-2-carboxylate as a vetrous oil (7.71 g, 40.5% yield, 85.0 A %).

$\delta_H$(400 MHz; CDCl$_3$) 8.31-8.26 (2H, m, Ar), 7.33-7.28 (2H, m, Ar), 6.94-6.76 (3H, m, Ar), 5.02-4.98 (1H, m), 2.98-2.81 (2H, m), 2.49-2.31 (2H, m); m/z (EI) 317.0698 (M$^+$.C$_{16}$H$_{12}$NO$_5$F requires 317.069954).

EXAMPLE 4

Synthesis of dimethylsulfoxonium-2-(6-fluoro-3,4-dihydro-2H-chromen-2-yl)-2-oxoethylide A 100 ml reaction vessel was charged with potassium t-butoxide (2.12 g, 18.91 mmol), trimethylsulfoxonium iodide (4.16 g, 18.91 mmol) and THF (30 ml) at 25° C. under nitrogen atmosphere. The slurry was protected from light with aluminium foil, heated to 70° C. and stirred at this temperature over 2 h. The mixture was cooled to 20° C. Separately a solution of 4-nitrophenyl 6-fluoro-3,4-dihydro-2H-chromen-2-carboxylate (2.0 g, 6.03 mmol) in THF (3 ml) was prepared and then added to the reaction mixture over the period of 1 h via syringe pump. The slurry was stirred for further 18 h and then quenched with demi water (14 ml). Ethyl acetate (40 ml) was added and the mixture diluted with further demi water (15 ml). The slurry was filtered to separate the suspended solid and the filtered liquid layers separated. The organic phase was washed with a saturated solution of sodium chloride (51 g), dried over anhydrous magnesium sulfate and concentrated in vacuo to furnish crude dimethylsulfoxonium-2-(6-fluoro-3,4-dihydro-2H-chromen-2-yl)-2-oxoethylide, as a vitreous oil (0.81 g, 48% yield).

$\delta_H$(400 MHz; CDCl$_3$) 6.83-6.79 (2H, m, Ar), 6.77-6.72 (1H, m, Ar), 4.92 (1H, bs), 4.45-4.39 (1H, m), 3.48 (6H, bs), 2.85-2.68 (2H, m), 2.29-2.21 (1H, m), 2.10-1.99 (1H, m); m/z (EI) 270.072598 (M$^+$.C$_{13}$H$_{15}$FO$_3$S requires 270.07252).

EXAMPLE 5

Synthesis of dimethylsulfoxonium-2-(6-fluoro-3,4-dihydro-2H-chromen-2-yl)-2-oxoethylide A 100 ml reaction vessel was charged with potassium t-butoxide (2.12 g, 18.91 mmol), trimethylsulfoxonium chloride (2.43 g, 18.91 mmol) and THF (30 ml) at 25° C. under nitrogen atmosphere. The slurry was protected from light with aluminium foil, heated to 70° C. and stirred at this temperature over 2 h. The mixture was cooled to 20° C. Separately a solution of 4-nitrophenyl 6-fluoro-3,4-dihydro-2H-chromen-2-carboxylate (2.0 g, 6.03 mmol) in THF (3 ml) was prepared and then added to the reaction mixture over the period of 1 h. The slurry was stirred for further 18 h and then quenched with demi water (14 ml). Ethyl acetate (25 ml) was added and the layers separated. The organic phase was washed three times with a saturated solution of sodium chloride (29 g, 30 g, 7 g respectively), dried over anhydrous magnesium sulfate and concentrated in vacuo to furnish crude dimethylsulfoxonium-1-(6-fluoro-3,4-dihydro-2H-chromen-2-yl)-1-oxoethylide, as a vitreous oil. (0.89 g, 52% yield).

$\delta_H$(400 MHz; CDCl$_3$) 6.83-6.79 (2H, m, Ar), 6.77-6.72 (1H, m, Ar), 4.92 (1H, bs), 4.45-4.39 (1H, m), 3.48 (6H, bs), 2.85-2.68 (2H, m), 2.29-2.21 (1H, m), 2.10-1.99 (1H, m); m/z (EI) 270.072598 (M$^+$.C$_{13}$H$_{15}$FO$_3$S requires 270.07252).

EXAMPLE 6

Synthesis of 2-chloro-1-(6-fluoro-3,4-dihydro-2H-chromen-2-yl)ethanone

A solution of dimethylsulfoxonium-2-(6-fluoro-3,4-dihydro-2H-chromen-2-yl)-2-oxoethylide (0.90 g, 3.26 mmol, 97.9 A %) in THF (12 ml) under mechanical stirring and under nitrogen was cooled to 0° C. and to this was added lithium chloride (0.179 g, 4.22 mmol). The methanesulfonic acid (0.267 ml, 4.03 mmol) was loaded dropwise at 0° C. in a 10 min. interval. The reaction mixture was heated to 20° C. in 10 min and then to 70° C. in a 30 min. interval. The reaction was kept under stirring for 2 hours at 70° C. and then cooled to 20° C. After 16 hours, a saturated aqueous solution of NaHCO$_3$ (10 ml) was added and strata were then separated. The organic phase was diluted with toluene (20 ml) and concentrated by reduced pressure to obtain a dry residue (0.78 g). This residue was dissolved again in toluene and washed with a saturated solution of NaHCO$_3$ (20 ml). The organic phase was further washed with demi water (20 ml) and brine (20 ml) and then dried under vacuum to give raw 2-chloro-1-(6-fluoro-3,4-dihydro-2H-chromen-2-yl) ethanone as a brown oil (0.66 g, 78% yield, 88.4 A %).

$\delta_H$(400 MHz; CDCl$_3$) 6.86-6.83 (2H, m, Ar), 6.80-6.75 (1H, m, Ar), 4.69-4.65 (1H, m), 4.63 (1H, d, J 16.8), 4.47 (1H, d, J 16.8), 2.91-2.72 (2H, m), 2.34-2.26 (1H, m), 2.13-2.03 (1H, m); m/z (EI) 228.035339 (M$^+$.C$_{11}$H$_{10}$ClFO$_2$ requires 228.03551).

EXAMPLE 7

Synthesis of 2-chloro-1-(6-fluoro-3,4-dihydro-2H-chromen-2-yl)ethanol

A solution under stirring of 2-chloro-1-(6-fluoro-3,4-dihydro-2H-chromen-2-yl)ethanone (0.33 g, 1.28 mmol, 88.4 A %) in ethanol (2.5 ml) was cooled to 0° C. under nitrogen. NaBH$_4$ (60.1 mg, 1.59 mmol) was added to the solution and the reaction mixture stirred for 2 hours. After checking that the starting product had disappeared by GC, the mixture was diluted with demi water (7 ml) and dichloromethane (7 ml) and the phases separated. The organic stratum was dried under anhydrous sodium sulphate, filtered and concentrated under vacuum to give raw 2-chloro-1-(6-fluoro-3,4-dihydro-2H-chromen-2-yl) ethanol as a mixture of diastereoisomers 54:46 (0.30 g, 70% yield, 67.9 A %).

$\delta_H$(4400 MHz; CDCl$_3$) 6.83-6.70 (6H, m, Ar), 4.21-4.16 (1H, m), 4.02-3.96 (1H, m), 3.94-3.88 (3H, m), 3.86-3.77 (2H, m), 3.74-3.68 (1H, m), 2.97-2.74 (4H, m), 2.30-2.21 (2H, b, —OH), 2.29-2.22 (1H, m), 2.02-1.96 (2H, m), 1.89-1.78 (1H, m); m/z (EI) 230.050989 (M$^+$.C$_{11}$H$_{12}$ClFO$_2$ requires 230.05067).

EXAMPLE 8

Synthesis of 6-fluoro-3,4-dihydro-2-(oxyran-2-yl)-2H-chromene 2-chloro-1-(6-fluoro-3,4-dihydro-2H-chromen-2-yl) ethanol (200 mg, 0.59 mmol, 67.9 A %) was dissolved in i-PrOH (5 ml) and THF (1 ml) under nitrogen and the reaction mixture cooled to 16° C. t-BuOK (102 mg, 0.87 mmol) was added and the reaction was stirred for 3 hours. The pH was then corrected to 7 with acetic acid and the mixture dried under reduced pressure. The residue was diluted with MTBE (12 ml) and washed with a saturated solution of NaHCO₃ (3×1.5 ml). The organic phase was dried with anhydrous sodium sulphate, filtered and concentrated under vacuum to give 6-fluoro-3,4-dihydro-2-(oxyran-2-yl)-2H-chromene as a mixture of diastereoisomers 54:46 (148 mg, 100% yield, 77.3 A %).

Diast. RR,SS: $\delta_H$(400 MHz; CDCl₃) 6.81-6.72 (3H, m), 3.88-3.82 (1H, m), 3.21-3.17 (1H, m), 2.89-2.76 (4H, m), 2.1-2.00 (1H, m), 1.97-1.87 (1H, m); Diast. SR,SR: $\delta_H$(400 MHz; CDCl₃) 6.84-6.73 (3H, m), 3.87-3.81 (1H, m), 3.15-3.10 (1H, m), 2.91-2.78 (4H, m), 2.18-2.10 (1H, m), 1.96-1.84 (1H, m).

EXAMPLE 9

Synthesis of 6-fluoro-3,4-dihydro-2-(oxyran-2-yl)-2H-chromene 2-chloro-1-(6-fluoro-3,4-dihydro-2H-chromen-2-yl) ethanol (2.5 g, 9.20 mmol, 84.9 A %) was dissolved in i-PrOH (25 ml) under nitrogen and the reaction mixture cooled to 0° C. To the solution was added a 2M aqueous solution of NaOH (12.5 ml) in 5 minutes and the reaction was stirred for 1 hour 30 minutes. The reactive mixture was then diluted with toluene (50 ml) and pH corrected with acetic acid (0.92 g). Further toluene (50 ml) and demi water (10 ml) were then added to the mixture and the phases separated after extraction. The collected organic phases were then washed with demi water (50 ml). The toluene phase was then anhydrified by azeotropic distillation and concentrated till dryness in rotavapor to give 6-fluoro-3,4-dihydro-2-(oxyran-2-yl)-2H-chromene as a mixture of diastereoisomers 52:48 (2.0 g, 96% yield, 86.1 A %).

Diast. RR,SS: $\delta_H$(400 MHz; CDCl₃) 6.81-6.72 (3H, m), 3.88-3.82 (1H, m), 3.21-3.17 (1H, m), 2.89-2.76 (4H, m), 2.1-2.00 (1H, m), 1.97-1.87 (1H, m); Diast. SR,SR: $\delta_H$(400 MHz; CDCl₃) 6.84-6.73 (3H, m), 3.87-3.81 (1H, m), 3.15-3.10 (1H, m), 2.91-2.78 (4H, m), 2.18-2.10 (1H, m), 1.96-1.84 (1H, m).

The invention claimed is:
1. A process for preparing a compound of formula

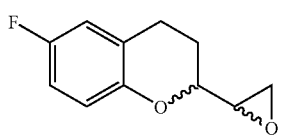

(I)

said process comprising steps a-c:
a. reacting a compound of formula

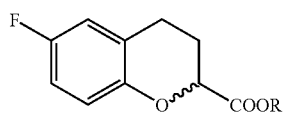

(IV)

wherein R is a ($C_1$-$C_6$)-alkyl group, optionally substituted aryl or optionally substituted heteroaryl, with dimethyl-sulfoxonium methylide to give the corresponding keto sulfoxonium ylide of formula

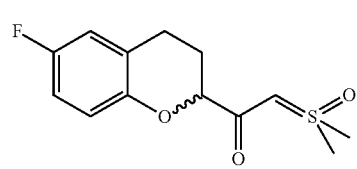

(V)

which is transformed into a compound of formula

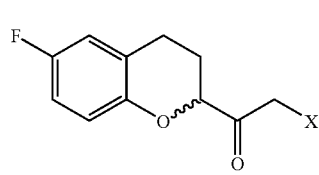

(II)

where X is halogen, by reaction with an anhydrous halogenhydric acid;
b. reducing said compound of formula II to give a compound of formula

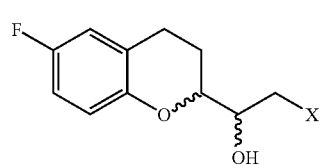

(III)

c. reacting said compound of formula III with a base to give the epoxide compound of formula I.

2. A process according to claim 1, wherein said step b is carried out by reacting a compound of formula II with sodium borohydride in the presence of an alcoholic solvent.

3. A process according to claim 1, wherein said step c is carried out by reacting a compound of formula III with alkaline alkoxides or hydroxides in the presence of alcoholic solvents or ethers or mixtures thereof.

4. A process according to claim 1, wherein said anhydrous halogenhydric acid is generated in situ.

5. A process according to claim 1, wherein said dimethyl-sulfoxonium methylide is prepared in situ from the corresponding sulfoxonium halide by reaction with a base in the presence of an organic solvent.

6. A process according to claim 4, wherein said anhydrous halogenhydric acid is anhydrous hydrochloric acid generated in situ by reacting lithium chloride with methanesulfonic acid in the presence of tetrahydrofuran.

7. A process for preparing a compound of formula

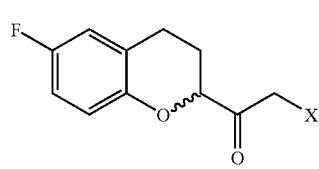

(II)

where X is halogen;

which comprises reacting a compound of formula

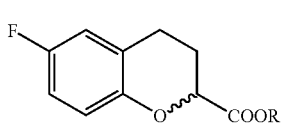
(IV)

wherein R is a (C$_1$-C$_6$)-alkyl group, optionally substituted aryl or optionally substituted heteroaryl; with dimethylsulfoxonium methylide to give the corresponding keto sulfoxonium glide of formula

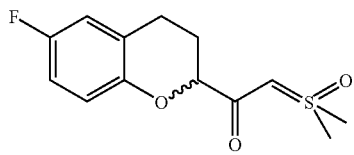
(V)

which is converted into a compound of formula II by reaction with an anhydrous halogenhydric acid.

8. A process for synthesizing nebivolol wherein the preparation of a compound of formula

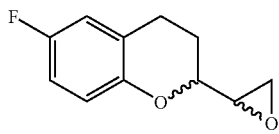
(I)

comprises steps a-c:
a. reacting a compound of formula

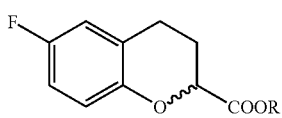
(IV)

wherein R is a (C$_1$-C$_6$)-alkyl group, optionally substituted aryl or optionally substituted heteroaryl, with dimethylsulfoxonium methylide to give the corresponding keto sulfoxonium ylide of formula

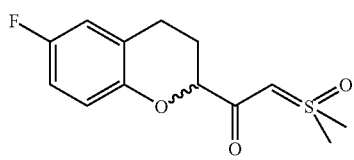
(V)

which is transformed into a compound of formula

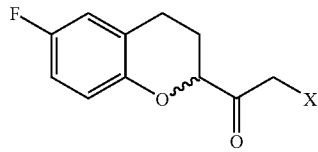
(II)

where X is halogen, by reaction with an anhydrous halogenhydric acid;

b. reducing said compound of formula II to give a compound of formula

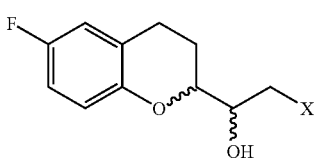
(III)

c. reacting said compound of formula III with a base to give the epoxide compound of formula I.

9. A process according to claim 1, wherein X is a chloride atom.

10. A compound of formula V dimethylsulfoxonium-2-(6-fluoro-3,4-dihydro-2H-chromen-2-yl)-2oxoethylide.

11. A process according to claim 7, wherein X is a chloride atom.

12. A process according to claim 8, wherein X is a chloride atom.

13. A process according to claim 1, wherein R is a substituted aryl or substituted heteroaryl.

14. A process according to claim 2, wherein said alcoholic solvent is mixed with water.

15. A process according to claim 7, wherein R is a substituted aryl or substituted heteroaryl.

16. A process according to claim 7, wherein said anhydrous halogenhydric acid is generated in situ.

17. A process according to claim 8, wherein R is a substituted aryl or substituted heteroaryl.

18. A process according to claim 8, wherein said anhydrous halogenhydric acid is generated in situ.

* * * * *